(12) United States Patent
Buchine et al.

(10) Patent No.: US 9,227,017 B2
(45) Date of Patent: Jan. 5, 2016

(54) AUTOMATIC MIXING DEVICE AND DELIVERY SYSTEM

(75) Inventors: Brent Alan Buchine, Watertown, MA (US); Christopher John Stepanian, Somerville, MA (US); Ralph Navarro, Shrewsbury, MA (US); Adam Richard Standley, Boston, MA (US)

(73) Assignee: Windgap Medical, LLC, Middlesex, MA (US)

( * ) Notice: Subject to any disclaimer, the term of this patent is extended or adjusted under 35 U.S.C. 154(b) by 531 days.

(21) Appl. No.: 13/529,757

(22) Filed: Jun. 21, 2012

(65) Prior Publication Data

US 2013/0178823 A1 Jul. 11, 2013

Related U.S. Application Data

(60) Provisional application No. 61/499,676, filed on Jun. 21, 2011, provisional application No. 61/597,161, filed on Feb. 9, 2012.

(51) Int. Cl.
| | |
|---|---|
| *A61M 5/20* | (2006.01) |
| *A61J 1/20* | (2006.01) |
| *B65B 29/10* | (2006.01) |
| *A61M 5/24* | (2006.01) |

(52) U.S. Cl.
CPC ............ *A61M 5/2066* (2013.01); *A61J 1/2093* (2013.01); *A61M 5/2033* (2013.01); *A61M 5/2448* (2013.01); *B65B 29/10* (2013.01); *A61M 2005/2073* (2013.01)

(58) Field of Classification Search
CPC ............ A61M 5/2033; A61M 5/2066; A61M 5/2425; A61M 5/2448; A61M 5/2459; A61M 5/282; A61M 5/284; A61M 5/286; A61M 2005/2013; A61J 1/2093; B65B 29/10
See application file for complete search history.

(56) References Cited

U.S. PATENT DOCUMENTS

| | | | | |
|---|---|---|---|---|
| 4,874,366 | A * | 10/1989 | Zdeb et al. | 604/518 |
| 5,354,278 | A * | 10/1994 | Kriesel | 604/132 |
| 5,451,214 | A * | 9/1995 | Hajishoreh | 604/235 |
| 5,531,683 | A * | 7/1996 | Kriesel et al. | 604/89 |
| 5,637,087 | A * | 6/1997 | O'Neil et al. | 604/82 |
| 6,562,002 | B1 * | 5/2003 | Taylor | 604/82 |
| 6,641,561 | B1 * | 11/2003 | Hill et al. | 604/136 |
| 6,685,693 | B1 * | 2/2004 | Casso | 604/500 |
| 7,678,073 | B2 * | 3/2010 | Griffiths et al. | 604/85 |
| 2002/0151842 | A1 * | 10/2002 | Gonnelli et al. | 604/70 |
| 2003/0012690 | A1 * | 1/2003 | Taylor et al. | 422/32 |
| 2005/0000514 | A1 * | 1/2005 | Sullivan et al. | 128/200.24 |
| 2008/0294100 | A1 * | 11/2008 | de Costa et al. | 604/84 |

* cited by examiner

*Primary Examiner* — Kami A Bosworth
(74) *Attorney, Agent, or Firm* — Ascentage Law, PLLC; Travis Lee Johnson; David S. Einfeldt

(57) ABSTRACT

A wet/dry auto-mixing injector having a mixing device containing at least one microfluidic channel for mixing or dissolving a dry component with a wet component stored in the injector device.

18 Claims, 14 Drawing Sheets

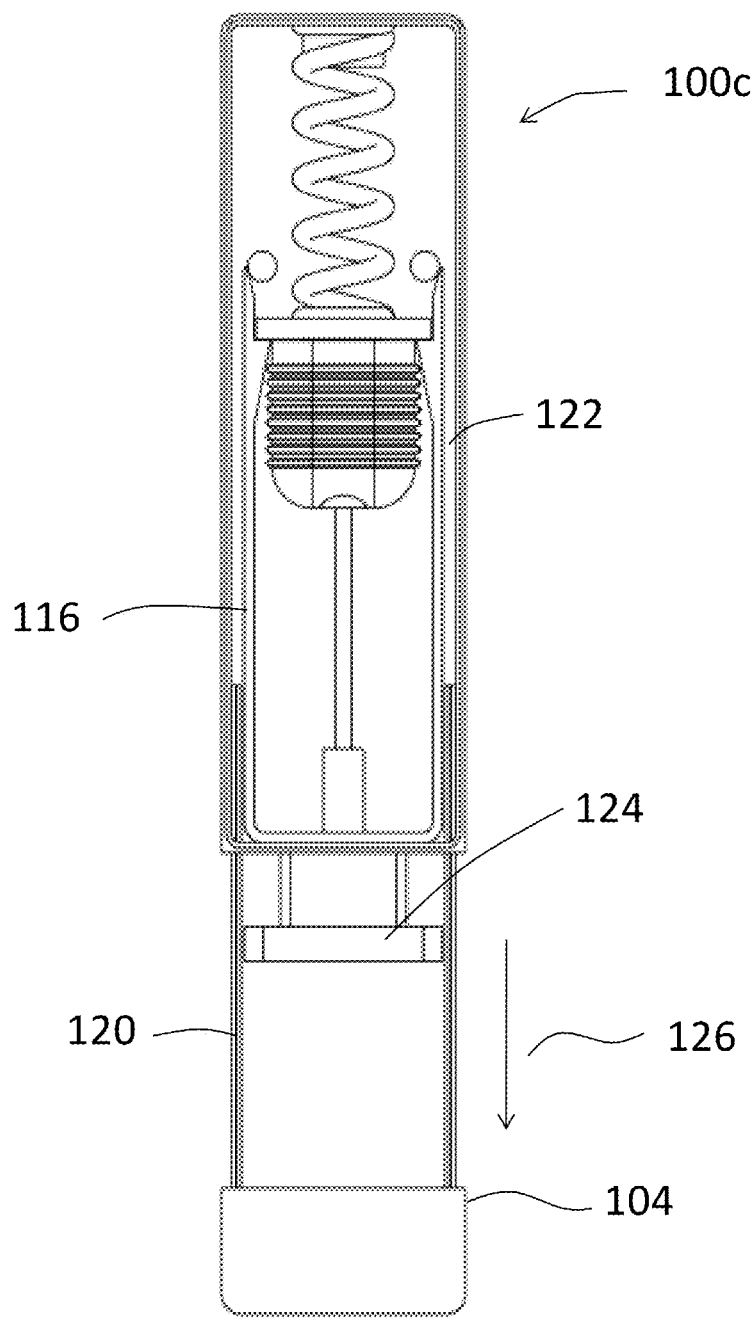
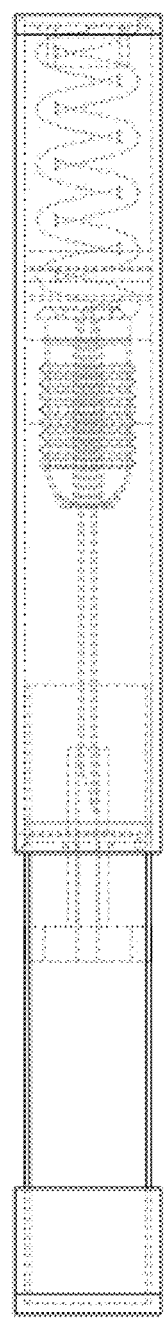
FIG. 1C
FIG. 1D

AUTOMATIC MIXING DEVICE AND DELIVERY SYSTEM

CROSS-REFERENCE TO RELATED APPLICATIONS

This application claims priority under 35 U.S.C. §119 to the following U.S. Provisional Patent Applications of which is hereby incorporated by reference in its entirety: U.S. Ser. No. 61/499,676 filed Jun. 21, 2011; and U.S. Ser. No. 61/597,161 filed Feb. 9, 2012.

COPYRIGHT STATEMENT

A portion of the disclosure of this patent application document contains material that is subject to copyright protection including the drawings. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

1. Field of the Invention

The present embodiments relate generally to auto-injectors and more particularly to wet/dry mixing auto-injectors, prefilled syringes and reconstitution devices.

2. Description of the Prior Art

Mixing systems and auto-injectors exist to mix wet and dry substances together and deliver those mixtures into a subject. However, current auto-injectors for mixing wet and dry components may be unable to completely dissolve dry components into a wet solution in a simple and easy to use manner. In many cases, multiple manual or mechanical inputs from the user are required to complete a reconstitution process and/or a waiting period of extended time may be required to dissolve the dry medicament. In addition, these systems are often bulky and difficult to transport or keep near an individual in need of a medicament delivery system.

The following application seeks to solve the problems stated.

SUMMARY OF THE INVENTION

A mixing and/or automatic injection device having an interior chamber containing a wet component that may be pH optimized to be mixed with a dry component contained in a mixing assembly. The wet component being confined or sealed in the interior chamber by a seal or valve, where upon activation of the seal or valve the wet interior chamber becomes in fluid communication with the mixing assembly and dissolution of the dry component into the wet component occurs. The mixing assembly can contain at least one fluidic conduit, for example at least one fluidic channel. In some embodiments, the mixing assembly contains at least one microfluidic channel. The mixing assembly is also configured to transfer the dissolved or reconstituted wet and dry components into a needle assembly or other delivery assembly configured to inject or deliver said components into a person or animal.

BRIEF DESCRIPTION OF THE DRAWINGS

FIGS. 1A-I illustrate an embodiment and various configurations of a wet/dry mixing auto-injector.

DETAILED DESCRIPTION OF THE PREFERRED EMBODIMENT

Figure 1A:
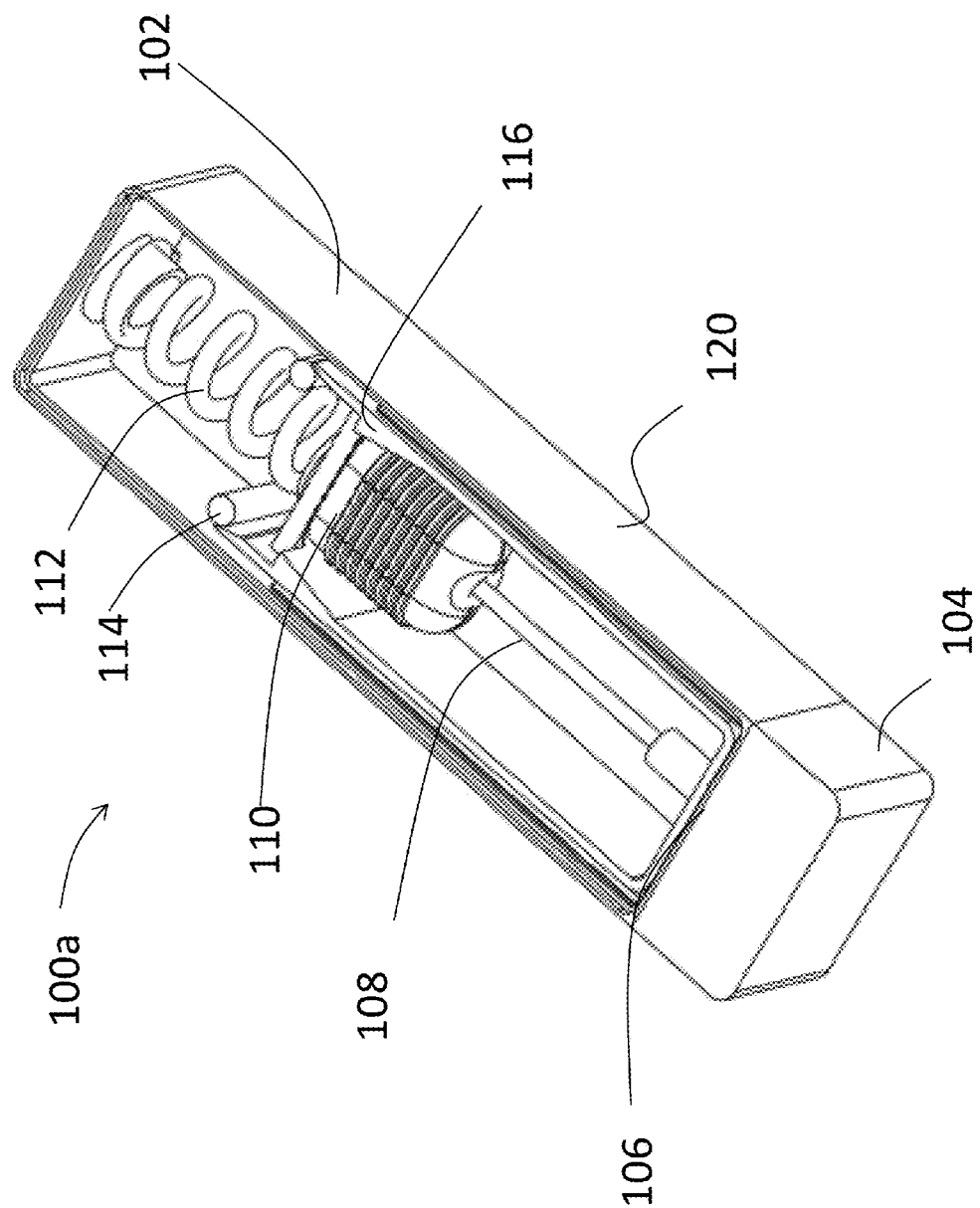

Aspects and embodiments described herein relate generally to the field of auto-injector devices, prefilled syringes and reconstitution devices. The following application describes an auto-injector and wet/dry mixing device configured to mix a dry and wet components of a medicament forming a solution to be injected into a person. This auto-injector device and mixing device is accomplished by integrating a mixing device assembly having at least one microfluidic channel into an auto-injector device with a pre-loaded charge or energy source such as one embodiment illustrated in FIG. 1A.

Some of the advantages of the mixing device assembly and auto-injector device embodiments described herein include compact size, mixing consistency, mixing speed, mixing control, eliminating shaking or swirling, increasing portability, filtering particulates. It also enables the use of dry medicaments, which allow for continued potency in broader temperature ranges.

For purposes of this application, a medicament may refer to any of a drug, medication, antidote, vaccine, protein, compound or other chemical substance. Medicaments may be formed of, or separated into multiple components such as wet and dry components that may be combined, reconstituted, or dissolved into one another to form a solution where the dry component or concentrated solution is soluble, partially soluble, or even non-soluble in the specified diluent and the wet component, solvent or solution, which dissolves or transports the active pharmaceutical dry component. This may be accomplished through solubility, pH, or other physical or chemical means. In addition, a medicament as described herein includes, but is not limited to, a dry form of epinephrine or adrenaline configured to dissolve into a solvent or solution through solubility, pH, or other physical or chemical means.

Exposure to certain substances, such as, for example, peanuts, shellfish, bee venom, certain drugs, toxins, and the like, can cause allergic reactions in some individuals. Such allergic reactions can lead to anaphylactic shock. This may also cause reactions such as a sharp drop in blood pressure, hives, and/or severe airway constriction, which may result in a life-threatening condition. Responding rapidly to mitigate the effects from such exposures may decrease chances for patient injury and/or death. For example, in certain situations, an injection of epinephrine (i.e., adrenaline) may provide substantial and/or complete relief from the allergic reaction. In other situations, an injection of an antidote to a toxin may greatly reduce and/or eliminate the harm potentially caused by the toxin exposure. Because emergency medical facilities may not be available when an individual is suffering from an allergic reaction or toxin exposure, some individuals carry a medicament delivery device, such as, an auto-injector, to rapidly self-administer a medicament to mitigate the reaction and/or effects.

The epinephrine and/or medicaments stored in auto-injectors as a liquid until ready for use, may suffer from certain shelf-life limitations and temperature, light, and oxygen exposure limitations and have a limited lifetime over which they are acceptably effective. Beyond that acceptable lifetime, these medicaments may degrade and lose an unacceptable amount of potency. In addition, degradation of epinephrine and/or other medicaments may be accelerated when subjected to large temperature excursions, especially when the temperature exceeds its acceptable storage temperature. For example, in order to maintain potency of epinephrine, some manufacturers recommend that an epinephrine auto-injector be stored at a controlled room temperature (20° C.-25° C. with allowable temperature excursions as low as 15° C. and as high as 30° C.). If this temperature range is maintained accurately, the epinephrine, may remain stable for up to 20 months from the date of manufacture, even though the manufacturer suggests the epinephrine and/or auto-injector be replaced after approximately 12 months of patient ownership, at a maximum. Any deviation of the epinephrine and/or auto-injector outside of this recommended temperature range will cause the epinephrine to lose potency possibly rendering the epinephrine ineffective more rapidly. This temperature, oxygen, material contact, compound instability, and/or light-induced degradation problem spans many liquid medicaments and markets in addition to epinephrine like Benadryl®, atropine, glucagon, butyrylcholinesterase, phinothiazemes, haloperidol, clozapine, fluphenazine, benzo diazepines, carbamazepines, nytroglycerin well as other small molecule and large molecule compounds. Potential markets served by this invention are allergies, psychotics, epilepsy, nerve agent antidotes, hypoglycemia, diabetes, chemical or biological warfare antidotes, migraines, pain killers, traumatic brain injury, dehydration, cardiac care, asthma, scurvy, small pox, or flu.

Maintaining the mandated storage environment for the medicament auto-injector may present a challenge for individuals not always carrying a temperature-controlled environment or near one. Often, individuals will keep epinephrine-filled auto-injectors in multiple temperature-controlled environments as a precautionary measure. However, an allergic reaction may occur physically distant from the nearest auto-injector. For example, bee stings, are more likely to occur outside than indoors. Food containing peanuts are more likely to be supplied to the individual away from a controlled home environment like at a baseball park. Emergency intervention required after a soldier is exposed to a chemical and/or biological toxin in the field, is also not likely to occur in a temperature-controlled environment. Merely placing an auto-injector in a purse, backpack, car and so forth is likely to encounter temperature excursions/fluctuations, outside of the recommended stabilized temperature range on a hot summer's day.

Currently, manufacturer's attempt to make individuals aware of the epinephrine's stability issues in part by allowing to the owner and/or user to see the liquid epinephrine through a clear window. The instructions state, "Replace if solution is discolored." In certain instances, an epinephrine filled auto-injector is observed only when an emergency situation has taken place. At this point, it may be too late to find a replacement medicament and/or device. Thus, a medicament solution and device that is less-temperature sensitive in addition to extending shelf-life is desired. Compact designs and portability are also desired for medicament delivery systems that will be carried on or near a person, such as in a pocket, in a small purse, on a keychain or on a necklace around ones neck.

One method of increasing the shelf life of medicaments is to freeze dry (lyophilize) and/or spray dry or vacuum dry and put them into dry and/or powdered form. This is, for example, done when shipping vaccines and/or other medicaments to countries where cold chain infrastructure is poorly implemented. Dry medicaments are then reconstituted into liquid form just prior to being dispensed into a syringe and injected into a patient. This helps to ensure that the medicament is fresh and potent.

One embodiment of an auto-injector device containing a dry and/or powdered medicament ("dry component") that is kept separate from the diluents ("wet component") is illustrated in FIGS. 1A-F. Upon activation of the device, the wet and dry components automatically mix together (without manual shaking or swirling required) and are subsequently injected into a human or non-human patient as a liquid dose. This mechanism of auto-mixing and auto-injection may occur in one, two, three or more simultaneous or subsequent steps.

Figure 1B:
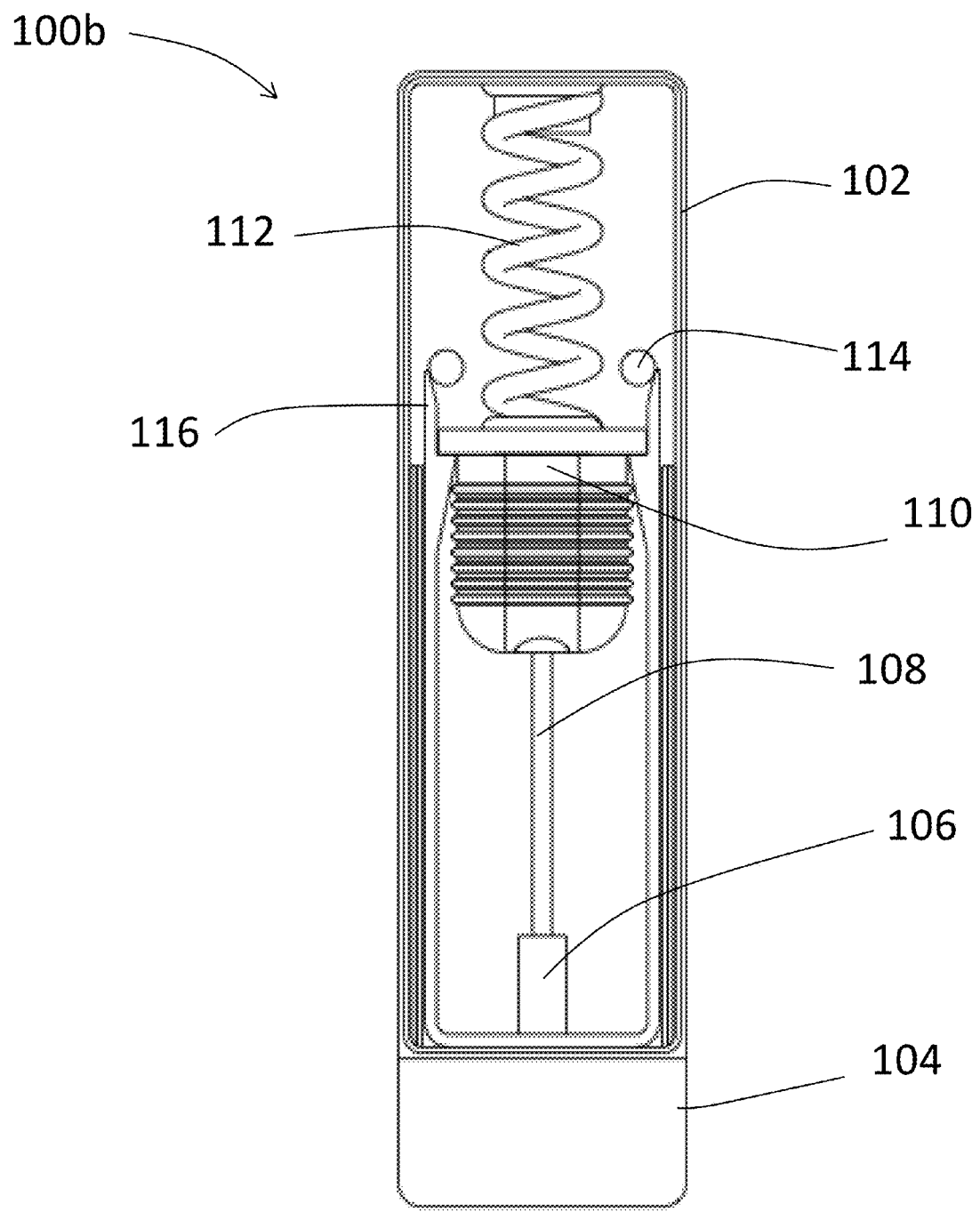

A perspective view of an embodiment of a wet/dry mixing auto-injector 100a in a stored state is illustrated in FIG. 1A. As illustrated, a front panel or side is removed to show the internal components of the auto-injector 100a. A housing 102 contains a pre-loaded spring 112 applying a force to mixing assembly 110, which is held firmly in place by a releasable latch 116. Extending from the mixing assembly 110 is a needle 108, which is partially contained in needle guide 106. A cap 104 is connected to safety shims 120 and may be separated from housing 102 by pulling cap 104 away from housing 102. Posts 114 are positioned near releasable latches 116 to spread the latches apart, which in turn allow the pre-loaded spring 112 to cause the mixing and needle assembly to move. A front view of the auto-injector 100a in storage mode with a removed front panel or side is illustrated in FIG. 1B.

Figure 1E:
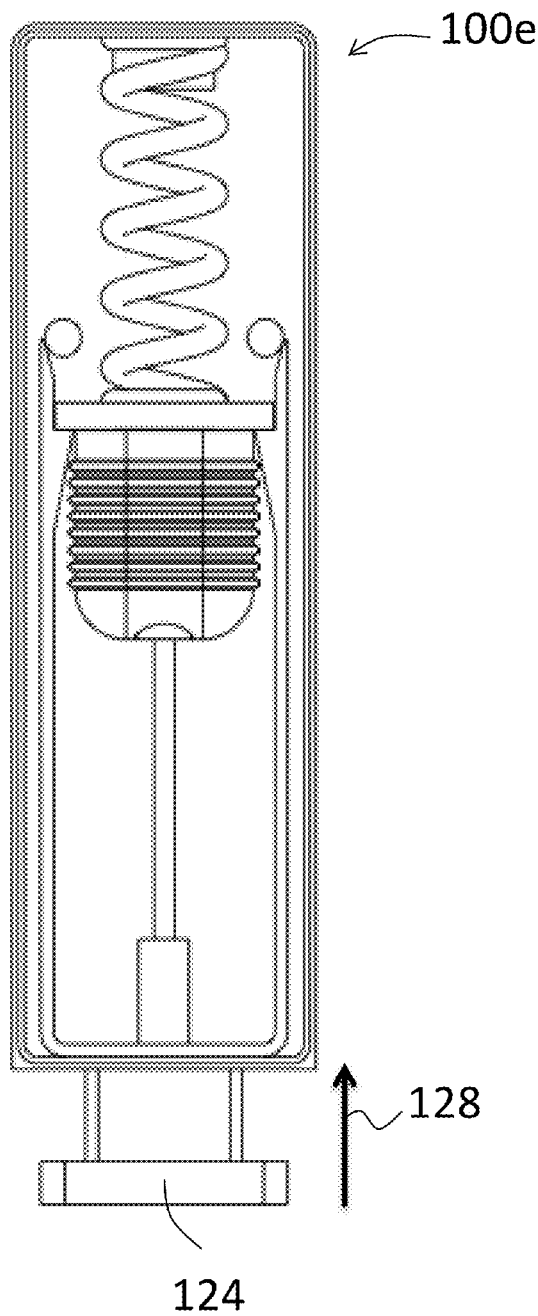
Figure 1F:
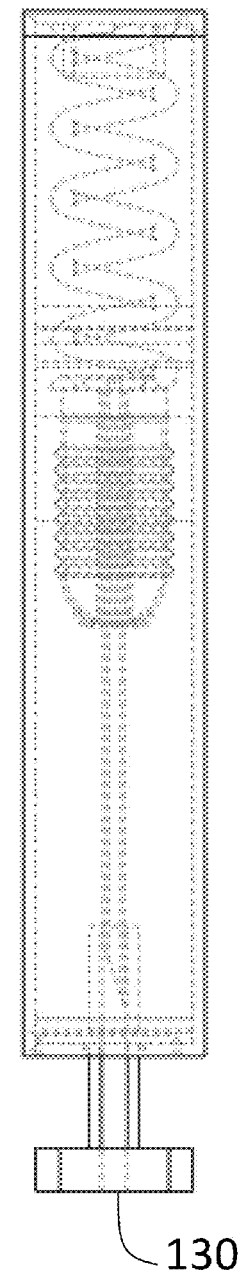

FIGS. 1C-D illustrates a wet/dry mixing auto-injector 100c where the cap and safety shim portion is being removed 126 to expose a gap 122 between the releasable latches 116 and the internal sides of housing 102, thus allowing for triggering mechanism 124 to be depressed (See FIGS. 1E-F). Triggering mechanism 124 may be attached or push up against releasable latches 116 causing them to spread apart around posts 114, thus releasing the stored energy in spring 112 to propel forward mixing assembly 110 with needle 108 through the needle guide 106. Stored energy sources may include compressed springs, compressed gas chambers, electric power or other storable energy sources known in the art.

As mentioned, FIGS. 1E-F illustrates wet/dry mixing auto-injector 100d where triggering mechanism 124 may be depressed or pushed 128 toward housing 102. One such scenario includes a person holding housing 102 in a hand and pressing or jamming triggering mechanism 126 against a leg. Again by pressing the triggering mechanism 124, releasable latches 116 are spread apart by posts 114 releasing the energy stored in spring 112 to force the mixing assembly 110 forward with needle 106 injecting into the leg.

Figures 1G, 1H:
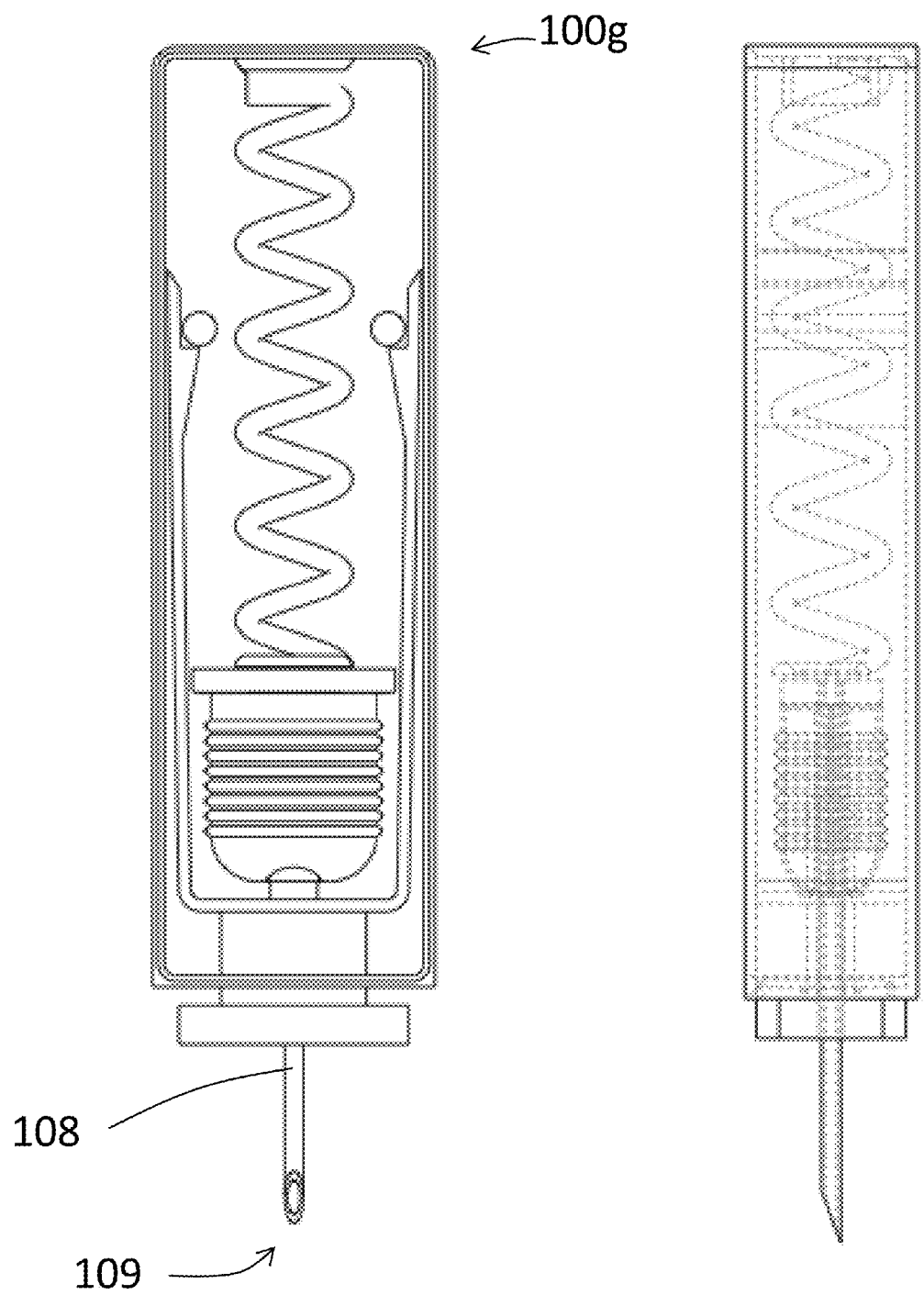

FIGS. 1G-H illustrate a the wet/dry mixing auto-injector 100g (in a triggered or fired state) with the needle 108 and exposed end 109 extended through needle guide 106 outside of housing 102, which may be injected into a person. The mixing assembly in some embodiments is comprised of a collapsible bulb containing a wet component. When the collapsible bulb is pressed against an inner side wall of housing 102, pressure builds inside the bulb to burst a seal separating the wet component in the bulb from a mixing device containing in part a dry component. Mixing then automatically occurs in the mixing device between the wet and dry components into a solution, which is then forced into needle 108 and into a person.

Figure 1I:
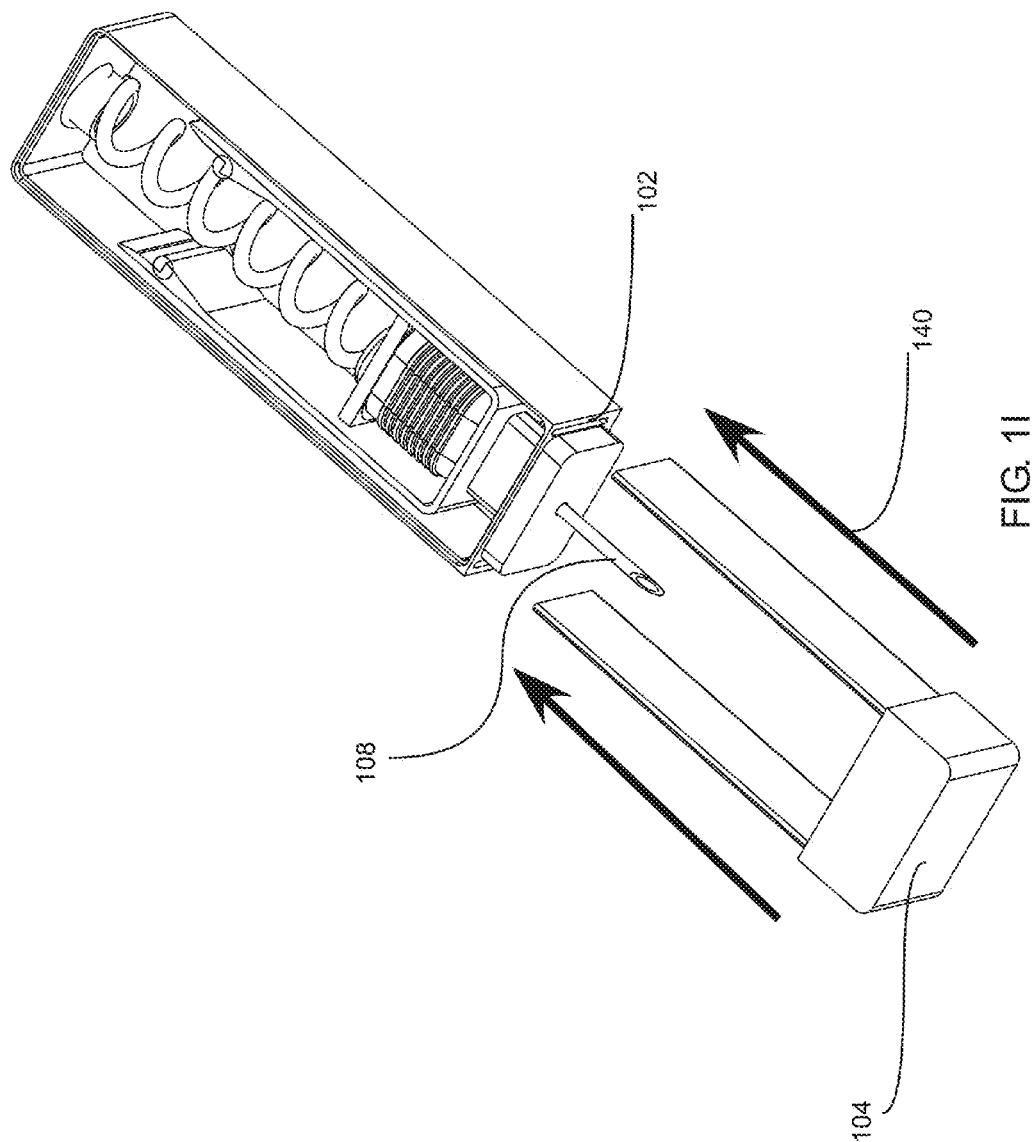

FIG. 1I illustrates a configuration of the wet/dry mixing auto-injector 100i having its cap 104 being reinserted 140 into the housing 102. This now allows the exposed needle 108 to be covered for safe handling.

Figure 2A:
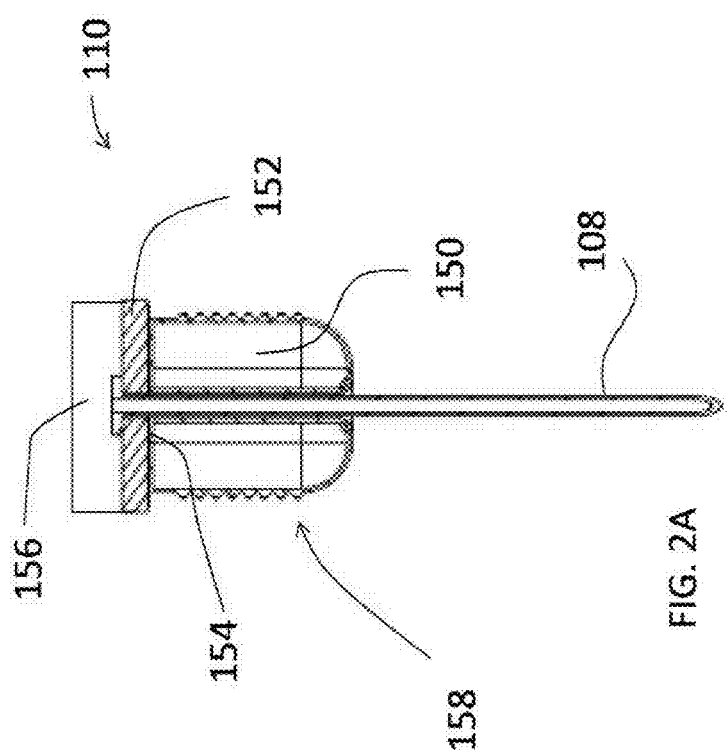
FIGS. 2A-F illustrate various embodiments of a mixing assembly.
Figure 2B:
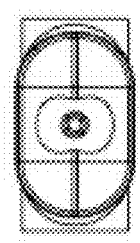
Figure 2C:
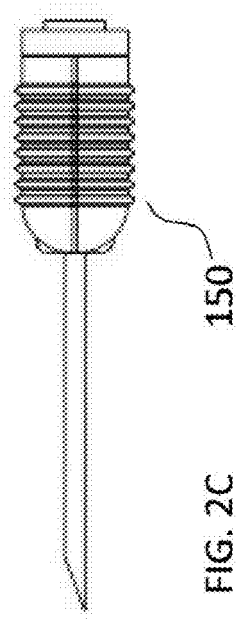

FIGS. 2A-C illustrate various views of a wet/dry mixing assembly 110 comprised of a mixing device 152, seal 154, wet component storage cavity 150 contained within collapsible bulb 158. Also shown in these views is a homogenization zone 156 that allows for the mixed wet and dry components to further homogenize prior to entering the needle 108. This homogenizing zone, which helps to remove any concentration gradients that may occur during the mixing process, is not required in all embodiments and may take many forms. For example, in one configuration that is devoid of a homogenizing zone the entrance orifice to the needle may be on the side of the needle, which is directly in fluid communication of the mixing device 152. As previously mentioned, a force such as a pre-loaded spring may act on the collapsible bulb creating a force on the seal separating the wet component from dry component contained within a portion of the mixing device. When the force is sufficient the seal may burst or open or move or change in some way, allowing the wet and dry components to be mixed in the mixing device.

In other embodiments not shown, a delivery assembly devoid of a needle is configured similarly to deliver the mixed solution into a person or animal. This may be accomplished through an IV that is already inserted, through the mouth, by pressure through the skin and so forth.

Automatic mixing is enabled by incorporating a micro-electrical-mechanical system (MEMS) device, microfluidic device, microfluidic chip, or series of micro or macro-fluidic channels or chips into the mixing device. There are many ways to incorporate these systems or devices into the mixing device 152.

Figure 2D:
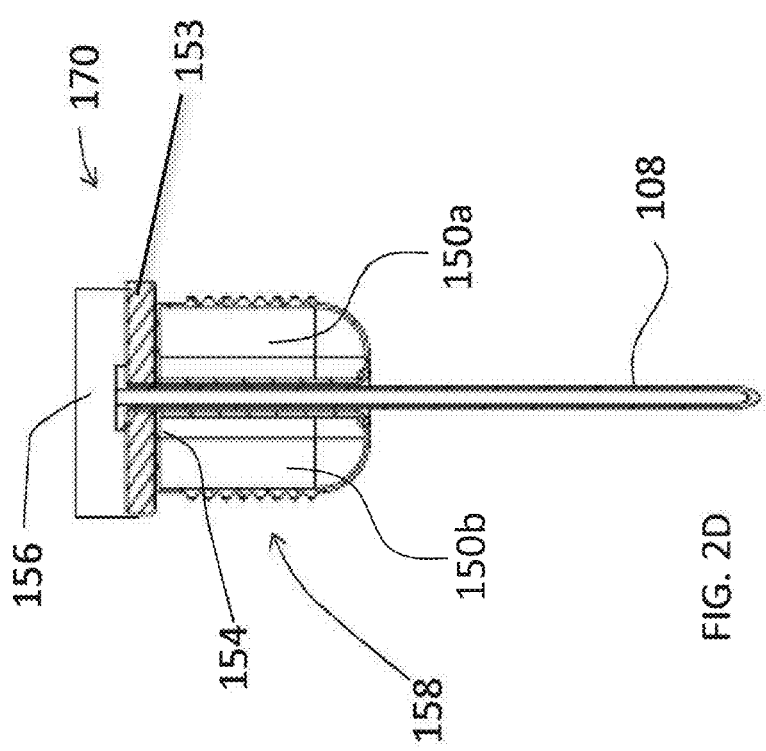
Figure 2E:
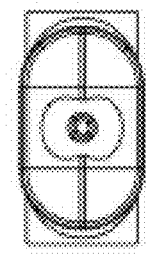
Figure 2F:
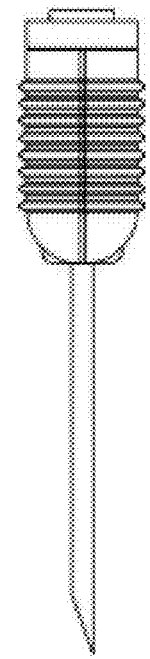

FIGS. 2D-F illustrate various views of a multiple wet/dry component mixing assembly 170 comprised of a mixing device 153 having multiple conduits or channels, seal 154, wet component storage cavities 150a-b contained within a collapsible bulb 158 and homogenization zone 156. Mixing assembly 170 allows for two different types of medicaments (or two doses of the same) to be mixed and inserted into a person using a single needle or other delivery system. In this embodiment seal 154 spans the orifices of each storage cavity 150a-b, which are each in fluid communication with a different channel contained within the mixing device 153. These channels may vary in length and size enabling a time mixing/release of each medicament. For example, a first wet component stored in 150a enters a unique channel(s) that have a pathway shorter than the unique channel(s) the second wet component stored in 150b are in fluid communication with. The first wet component mixes with the first dry component, homogenizes (in this embodiment, but not all embodiments), enters the needle assembly and is injected into a person, where the second wet component takes longer to mix with the second dry component and follows after the first mixed medicament has entered the needle assembly to be injected into the person after. This is useful for two medicaments that are not compatible to be stored in the same portions of the mixing assembly and/or reconstituted or mixed together in the same channel. Mixing assembly 170 may be used with a single pre-loaded force, multiple pre-loaded forces and a single delivery system.

Figure 3A:
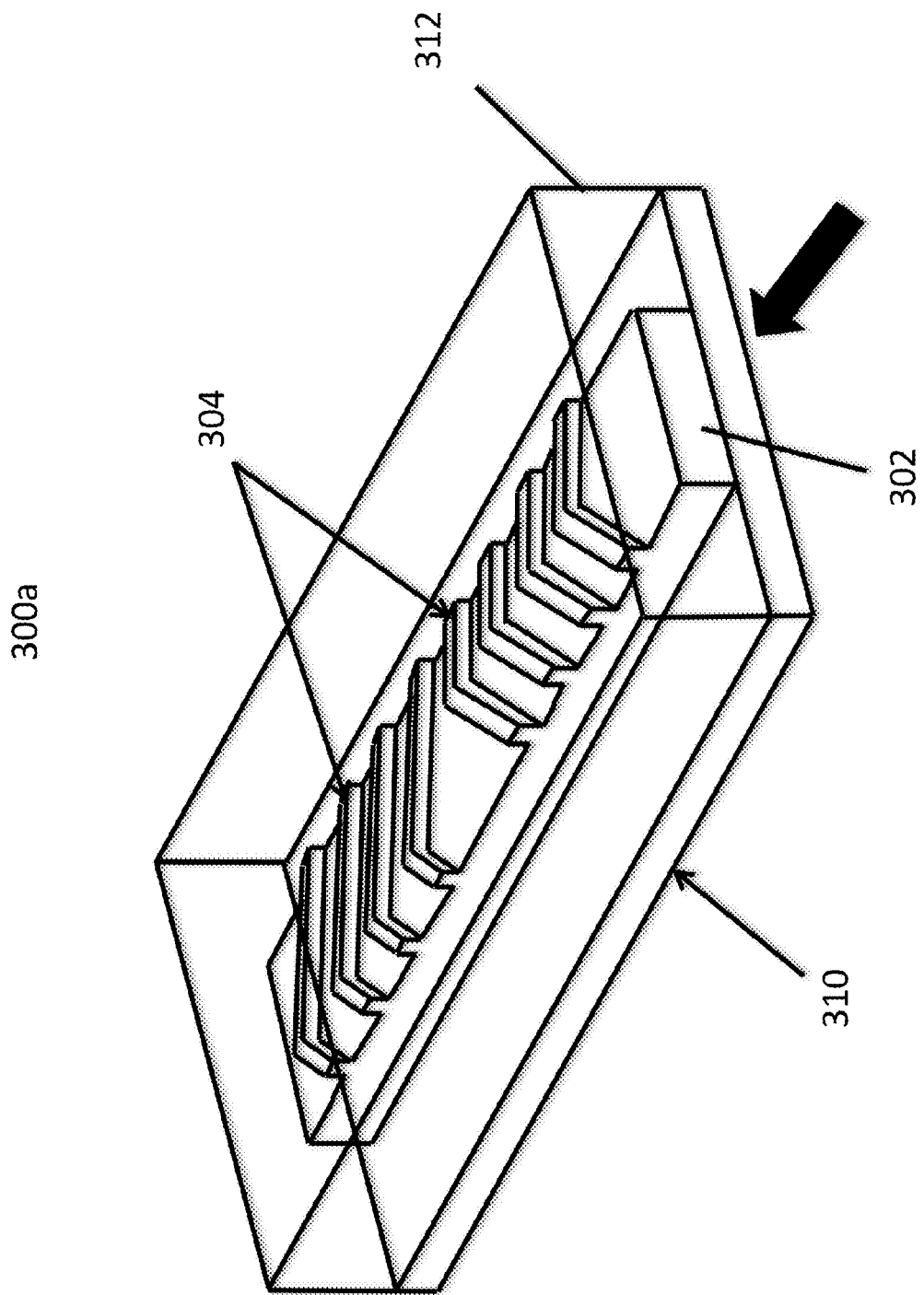
FIGS. 3A-G illustrate various microfluidic channel configurations for use in a mixing assembly.
Figure 3B:
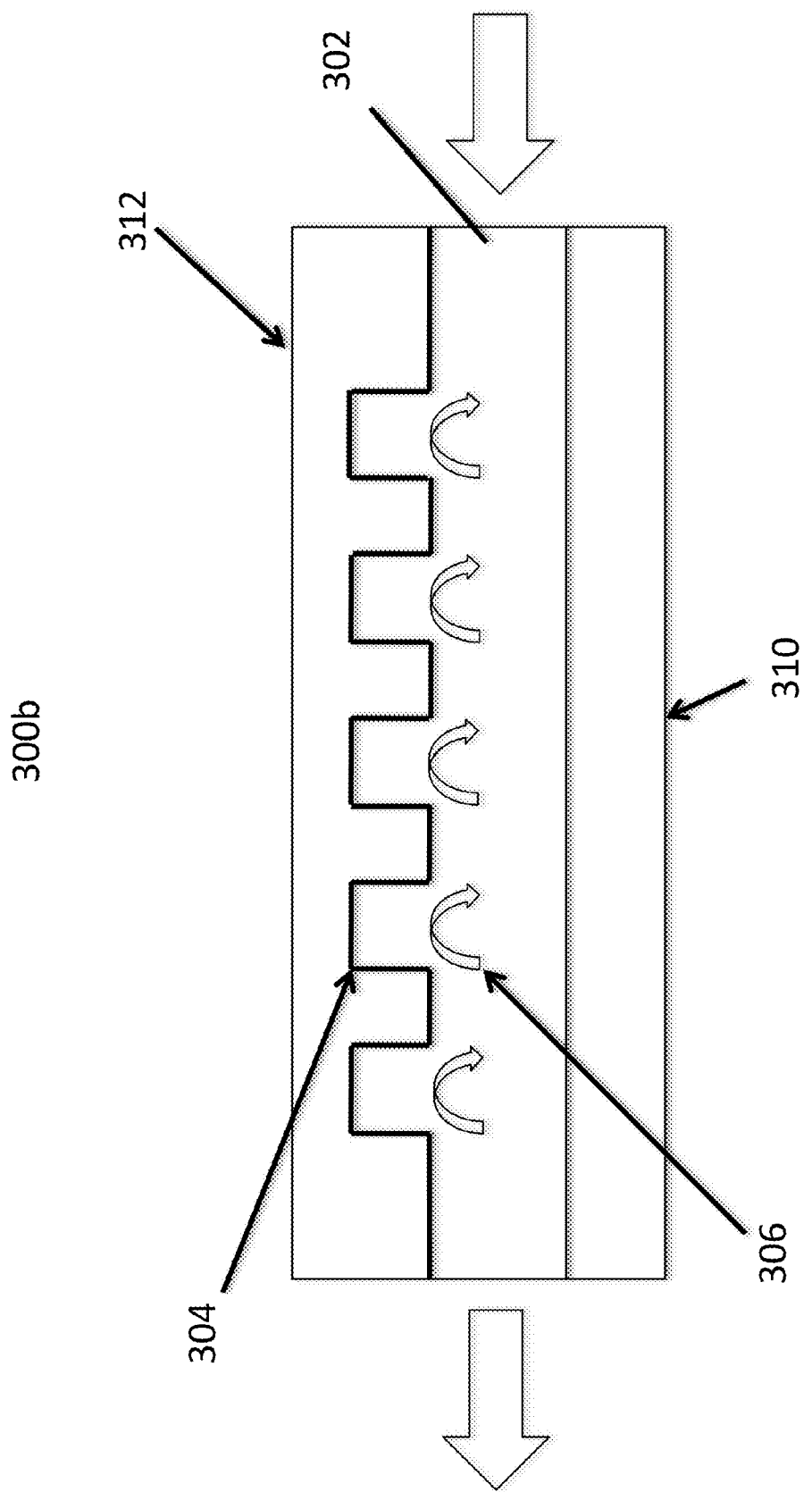

Microfluidic devices or systems enable control and manipulation of fluids at very small scales. At sub-centimeter and/or sub-millimeter dimensions, the role of interfaces starts to become dominate and surface tension, fluidic resistance and such begin to control behavior, which may respond differently than macroscopic properties of fluid flow. Mixing can be accomplished with systems similar to the one drawn in FIGS. 3A-B. In these figures, a main flow channel 302 is machined, for example, in glass or polymer with a series of "herringbone" or other type of grooves 304, which create an environment causing the flow of material through the channel to be chaotic as opposed to laminar. This chaotic flow creates a series of eddy's or vortices inside the channel, which function to stir or mix and dissolve dry components into the wet component forming a solution.

Embodiment 300a may be made of two parts, such as machined portion 312 where the main channel 302 and grooves 304 having an alternating pattern (these grooves may also be randomized) are all formed therein. 312 may be constructed of machined glass or an injection molded polymer. A base 310 that is a flat glass or polymer is then attached to 312 enclosing the main channel 302. Similarly, the cross-sectional view of embodiment 300b has the manufactured portion 312 having both the main channel 302 and grooves 304 formed therein, which is attached to a base 310. Chaotic flow here is illustrated by 306.

Figure 3C:
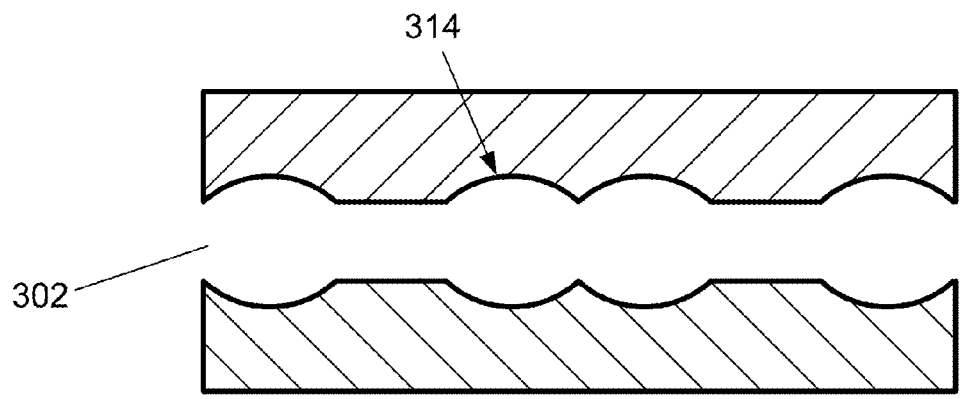
Figure 3D:
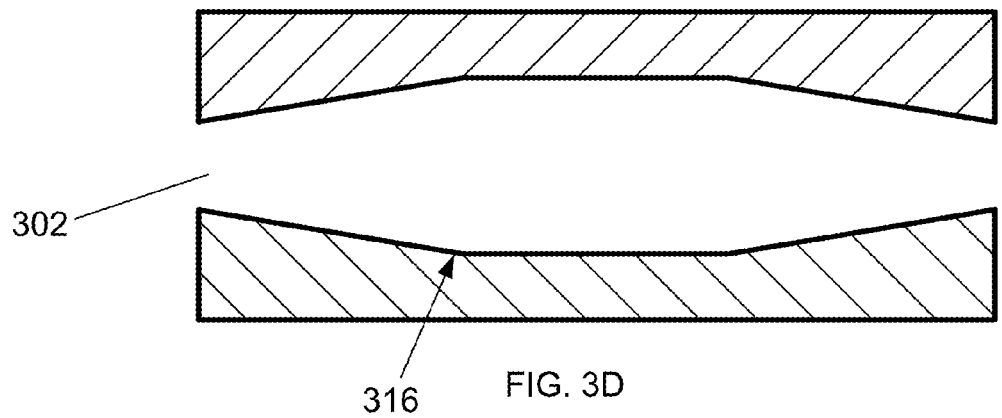

Alternatively, the flow channel may be constructed to widen and narrow or bulb/bulge along one side, two sides or around the entire cross-section of the channel. For example FIG. 3C illustrates a flow channel having multiple bulbs 314 integrated into the main flow channel 302, which help to break up laminar flow and cause chaotic flow behavior. In this cross-sectional view, the bulbs 314 are shown to be on the top and bottom of the channel, but may also be formed around the entire cross-section of main channel 302. FIG. 3D illustrates a micro-channel that gets wider and smaller, which also may be useful in converting laminar flow to chaotic flow within the flow channel. Here the main channel 302 is initially smaller in width and then expands in width to a swell 316. Swell 316 in other configurations may act as a reservoir or well and have larger amounts of dry component stored therein. Again swell 316 may be a larger pocket or open area in which smaller structures may be placed within, the swell and any contained structures therein help cause disruption of flow. Swells or wells may be placed strategically through a micro-channel system to create mixing.

Figure 3E:
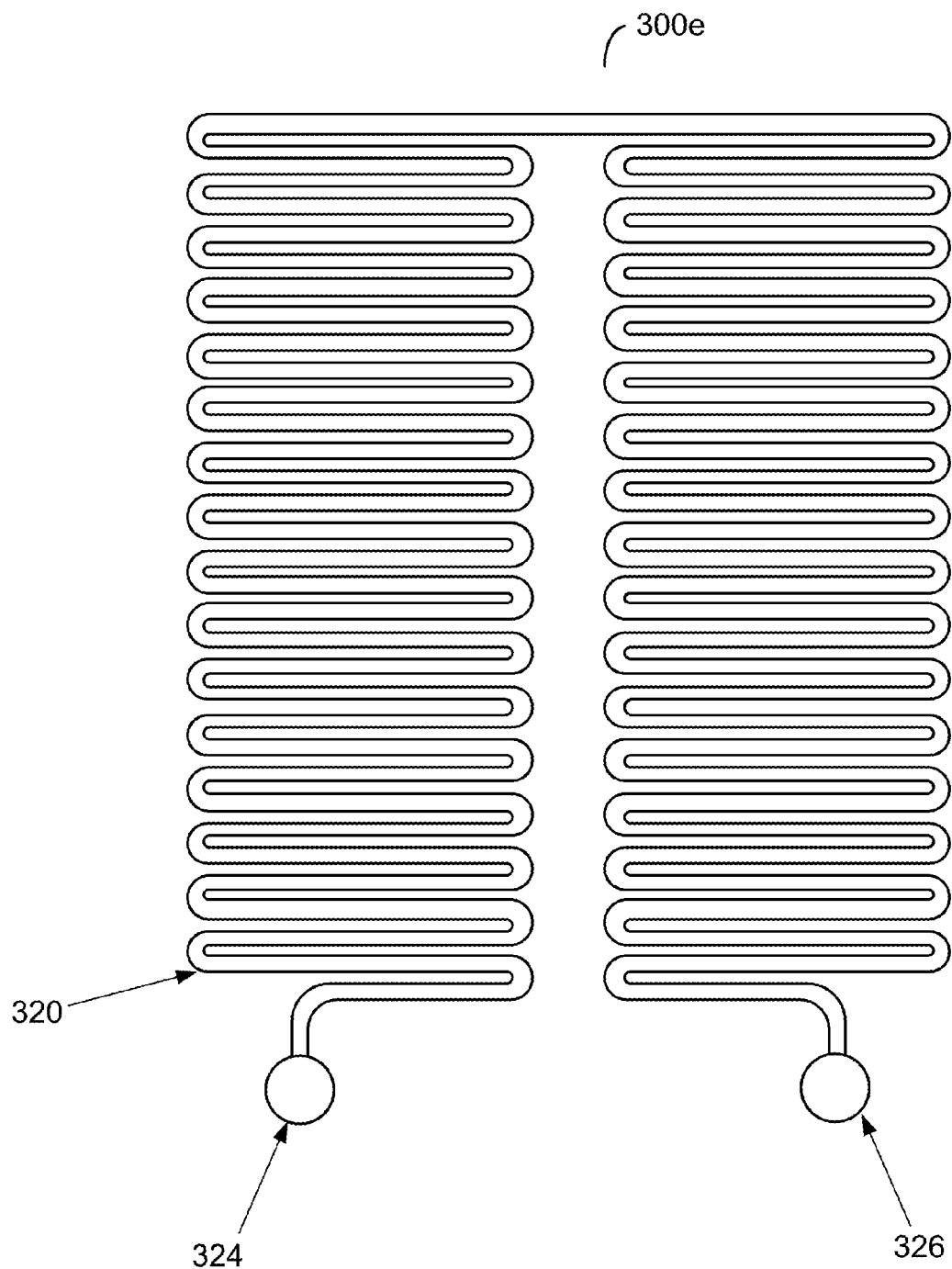
Figure 3F:
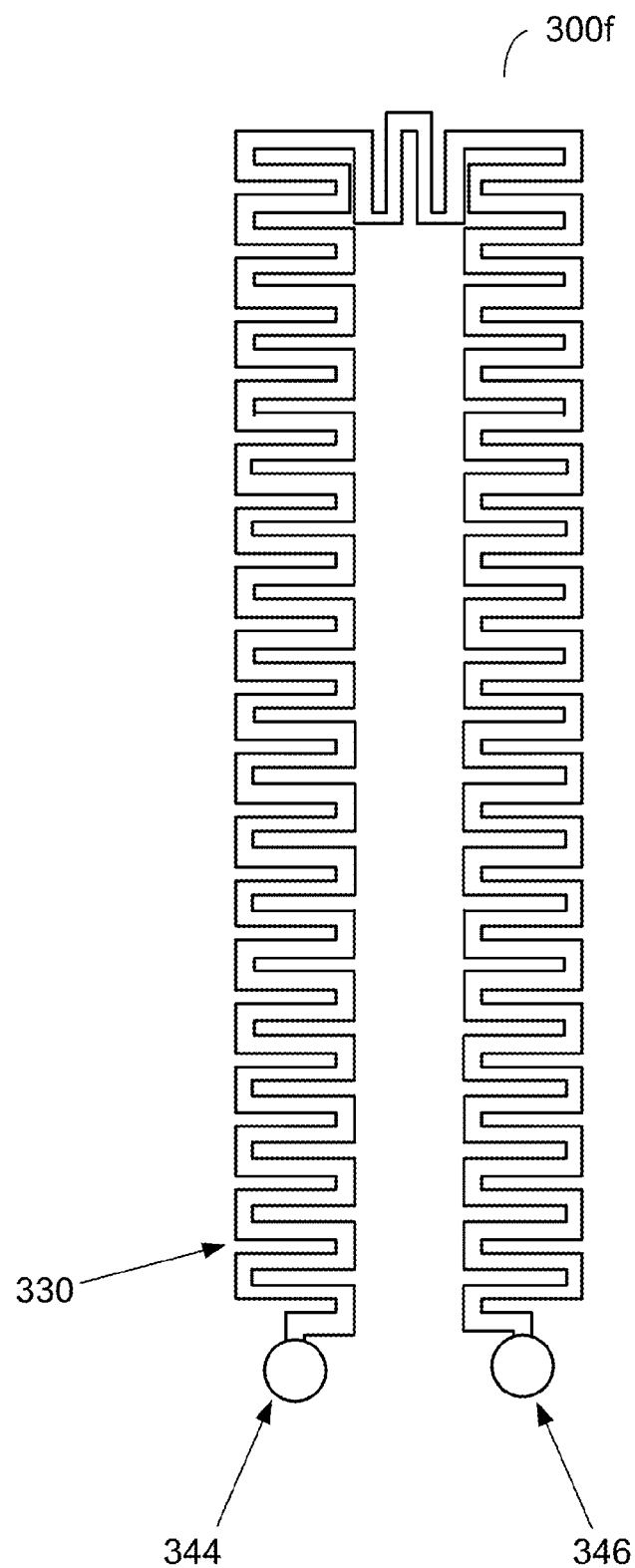
Figure 3G:
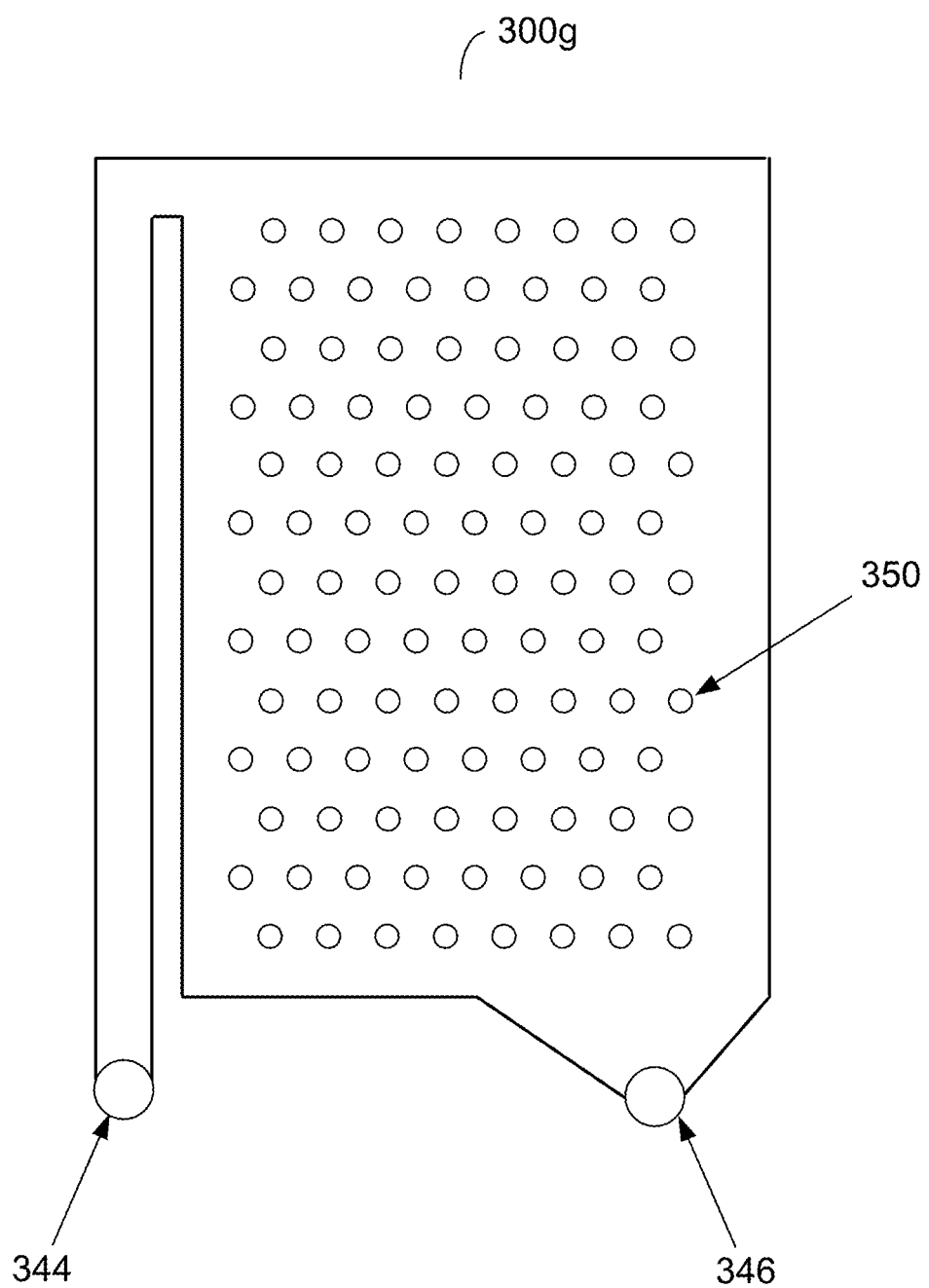

Another way of creating chaotic flow and mixing is to introduce bends or turns into the micro-channel(s) of the mixing device such as using a serpentine channel shown in FIGS. 3E-F rather than a straight channel, varying width or herringbone design. These serpentines have two functions. First, they enable miniaturization of the plumbing by bending the fluid flow direction so that the channel can double back, thus a longer channel more efficiently utilizes a smaller area. Second, natural flow becomes disrupted every time there is a bend or elbow in the channel, which results in mixing. These serpentine meanders can be designed so there are soft turns 320 that snake back and forth (shown in embodiment 300e), or they can be designed with sharp 90 degree bends 300, which is shown in 300f. They can even be designed so that the bend exceeds 90 degrees (not shown) that forms a more saw-like tooth pattern. Each embodiment will result in different mixing properties that can enable control over the quantity and quality of mixing. This may be important given that certain drug compounds can be damaged if mixing is too aggressive whereas other compounds may require a more aggressive mixing device. This variability in tuning the mixing conditions allows for a variety of wet/dry components to be used in a compact auto-mixing injector device as control is one key performance attribute of the present application. In each of these microfluidic embodiments 300e-f each is comprised of single channel having an opening 324, 334 to receive a wet component after the seal has been activated to an open or mixing state and an exit 326, 336 configured to be in fluid communication with a needle assembly or an in-between homogenization region.

In another configuration, a straight microfluidic channel configured with parallel walls may be sufficient to mix wet and dry components. Dry components stored inside a portion of the microfluidic channel may act to break up the laminar flow within the channel and create chaotic mixing. When the liquid moves through the channel and begins to push into the dry component contained in a portion therein, the flow front will cause natural turbulence or chaotic flow that focuses the flow towards the center of the channel and then causes the liquid to double back in the reverse direction near the channel wall. In order to make this happen, the channel dimension, which, in one embodiment can be defined by a square cross-section, should be below a certain size. For this embodiment and many of the embodiments described herein, one or both sides of the channel cross-section may have a dimension less than 2 mm, or between 1 mm and 2 mm, or less than 1 mm, or between 500 um and 1 mm, or less than 500 um, or between 250 um and 500 um, or less than 250 um, or between 100 um and 250 um, or less than 100 um, or between 50 um and 100 um, or less than 50 um, or between 10 um and 50 um, or less than 10 um, or between 1 um and 10 um, or less than 1 um. For purposes of this application, channels having a channel with a cross-sectional dimension less than 1 um are considered to be nanofluidic and have their respective set of properties for mixing medicaments. For a herringbone or groove embodiment, the dimensions of the grove-like-cuts are defined in a model which is in the public domain and published in Whitesides et al., Science, V295, 2002. Channel cross-section shapes include but are not limited to circular, elliptical, square, rectangular, and so forth.

The single channel serpentine microfluidic configurations for a mixing device shown in FIGS. 3E-F are generally constructed in a planar configuration comprising of a long channel where most of the bends occur in a single plane. In other embodiments not shown a non-planar microfluidic channel configuration where the microfluidic channel(s) may be positioned with bends and flow direction in multiple planes is contemplated. Another multi-dimensional configuration (not shown) includes using a microfluidic channel that is not confined in a rigid space, such as a bendable or flexible tube that may be repositioned or move as fluid passes through, which also may assist in the mixing process.

FIG. 3 illustrates a mixing channel 300g having an opening 344 leading around a bound into a well or larger interior portion of the channel where internal structures such as posts 350 are contained therein to facilitate chaotic flow and mixing. Here channel 300g funnels back into an exit/opening 346. The posts may be on the nano-scale in size or even the micro-scale in size. Various internal patterns and shapes assist in causing chaotic flow and mixing. Some channels may include multiple portions having internal structures.

At the micro-scale, mixing may also be accomplished with active assistance from additional forces like electric fields, magnetic fields, acoustics and such. For example, a voltage can act on a charged solution or electric-double-layers that form at the interface between the channel sidewall and the fluid itself. This voltage can be used to cause mixing.

Manufacturing a mixing device may be done in a variety of ways. One common way is with SU8 lithography and PDMS. First, SU8 2100 series from Microchem is spun on a wafer and baked at 65 C for 5 min and then at 95 C for 20 min on a hotplate. The substrate is removed from hotplate and allowed to cool. Photolithography is done by exposing the SU8 through a mask of the desired pattern at 540 mJ/cm2. The exposed SU8 is then baked at 65 C for 10 min and 95 C for 5 min. Once this is done the wafer is cooled and developed in PGMEA for 10 min. Once the pattern has been revealed, this can be used as a master from which to replicate microfluidic channels in silicone or PDMS. For example, PDMS is mixed with a curing agent and then cast on top of the master fabricated in SU8. It is good to silinize the master for up to 3 hours using 1H, 1H, 2H, 2H-Perfluorooctytrichlorosilane before casting the PDMS to ensure good release. Once the PDMS is mixed and cast it is put into a vacuum to remove the bubbles and then placed into a drying oven at 65 C for more than 5 hours. Once drying is finished it can be peeled from the master and bonded to another block of PDMS or glass. This bond may be made by activating both surfaces with an oxygen plasma. It may be necessary to make holes in the PDMS or glass in order to create inlets and outlets for fluid flow. Another embodiment of microfluidic fabrication can be demonstrated by machining into glass. Again, photolithography can be used to define a pattern and then dry and/or wet etching processes like reactive ion etching or hydrofluoric acid respectively can be used to transfer the pattern into the glass. Ultrasonic machining and direct write using a laser is another way to make these channels in glass substrates. Once the channels are machined into a piece of glass, a complete and sealed glass mixing device can be fabricated by bonding two glass parts together using a process called fusion bonding.

Another embodiment of the fabrication can be done using injection molded plastics and/or other methods of shaping plastic parts like embossing. The plastic mixing devices may be sealed to either glass or other plastics using a variety of techniques including thermal sealing, sonic welding or epoxy.

The dry component may be stored in a variety of locations inside or outside the mixing device including in chamber(s), pocket(s), a portion of the micro-channel(s). In one configuration, the dry component is placed into the mixing device wet and subsequently dried. For example, epinephrine or another medicament is dispensed into the device wet, lyophilization or some other controlled drying technique is performed to dry the epinephrine component inside the mixing device where it resides in a more stable state until a wet component enters therein and mixing, dissolution or reconstitution begin. When manufacturing the injection or mixing device the wet component may be inserted into the mixing assembly, but confined or sealed off in a separate region, blister, chamber, vial, collapsible bulb by a seal, valve or other temporary restraining mechanism until it is ready to be activated, mixed with the dry component and used or injected into a person or animal. In this separation state, as mentioned the components are able to have an increased shelf-life and/or temperature exposure range. Upon activation, the mixing of the wet and dry components would take place inside the mixing assembly before injecting or dispensing the drug inside the individual.

In a configuration, where the dry component is stored inside the mixing assembly, techniques such as spray drying, powder fill, vacuum drying or other method of inserting a dry powder form therein may be used. These dry component adding techniques may be used in the microfluidic channels, swells, homogenization zones and other areas within the mixing assembly.

In some configurations, multiple dry components may be inserted or contained in the mixing assembly. For instance, a first dry component may aid in dissolving with the second dry component after it is dissolved or partially dissolved with the wet component. It is also contemplated that multiple wet chambers, each with a different wet component, may incorporated into the automatic injection device.

Some formulations of wet and dry components include, but are not limited to, one or more therapeutic compounds (e.g., adrenaline) dissolved in an appropriate solvent. In some embodiments, the solvent is an aqueous solution. The aqueous solution can be water alone, or can include one or more buffers, salts, and/or other components. The pH and/or salt concentration of the solvent can be optimized for solubilizing the therapeutic compound(s). In some embodiments, the solvent is or includes an organic solvent (e.g., an alcohol). The dry component may also be any dry form of a medicament including the base and any salt forms. For example free base epinephrine as well as any epinephrine salts including: HCl, maleate, malate, fumarate, bitartrate, acid tartrate, hydrogen tartrate, and other salts may be used as the dry component.

The barrier or seal serves to prevent un-intentional mixing and/or humidity from the surrounding environment from penetrating the dry storage and degrading the medicament. Upon activation of the device, a spring and/or mechanical arm and/or pressure and/or some type of flow will push through the barrier and/or break the barrier and/or the barrier will move and/or change in some way to allow the wet liquid component to interact with the dry resulting in the dry component becoming soluble and/or dissolving in the wet component. A barrier separating the wet component from the mixing assembly containing an orifice, o-ring, and/or separating barrier made of a material such as, rubber. Flow will continue and a secondary mechanism may be activated, thus causing the two components to move through the mixing device so that sufficient, complete, uniform, and/or homogeneous mixing takes place. The applied force causes the freshly mixed solution through the needle, syringe, and/or other delivery mechanism, which results in the drug entering the body of a human or non-human. This configuration may be used where the dry component is stored in a chamber or pocket prior to entering a microfluidic channel or within a portion of the microfluidic channel(s) itself.

It is also possible to use microfluidic pumps based on electro-osmotic flow and or piezoelectric pumps to serve as the mechanism by which the fluid is driven into and/or out of the mixing device and/or needle.

Pumping may also be enabled by actuating a sealed blister containing the liquid component of the epinephrine. The blister can either be separate or incorporated into the plastic or glass of the mixing device. The blister commonly consists of a round, fluid-containing pocket with one stiff face and a flexible bulged membrane. The bulged membrane commonly is formed of a multiple layer laminate that includes an entrained metallic layer to decrease the rate of long-term moisture transport out of the blister. This metallic layer would not be in direct contact with the medicament. The stiff face may be solid or contain a membrane designed to allow for the exfiltration of the blister's entrained fluid upon a certain pressure being attained. Upon need, the blister is pressurized and/or collapsed by actuating the blister by electrical and/or mechanical and/or chemical, and/or thermal means. This pressure and/or applied force is sufficient to cause the controlled evacuation of the blister and allow the contained fluid to move within the device to where it is used and/or mixed. The actuation may be accomplished by the use of a memory metal such as Nitinol to actuate the bulged membrane and generate sufficient pressure to evacuate the blister and move that fluid through subsequent dry drug components and mixing structures. Other actuating devices such as linear actuators and motors may be used to actuate the blister.

The device may be either powered by an electro-chemical storage device such as a capacitor or battery and/or a mechanical storage device such as a compression or torsion spring. If the device is powered by an electro-chemical storage device, additional features may be added such a microcontroller to enable device function, provide feedback to the user, and/or provide feedback to the manufacturer. User feedback may be in the form of audio and/or mechanical and/or visual cues and/or electromagnetic signals such as information using Zigbee and/or internet protocols (IP) and/or Bluetooth protocols.

In addition to, but separate from, stabilizing the medication and/or antidote, the design goal of the device would be to make it as similar as possible in design to an existing and well-understood device commonly in use by its users. The current devices are based upon unique designs with either minimal or counter-intuitive relationships with the life experiences of their user base. An example of this problem in current devices would be the design of an auto-injector to resemble a pen but to require the user to use that pen-like auto-injector in a manner different than what the user associates with a pen.

Size is an issue when it comes to auto-injectors. More than 50% of the owners of the devices do not carry it with them. One aspect of this problem is size. A compact auto injector may make it more likely that the users will carry it with them. Common epinephrine auto injector case sizes are about 6"×1.5"×1", making them difficult to carry without a custom carrier or secondary carrying device like a purse and/or backpack and/or other container. A smaller device that could be attached to a key chain and/or easily fit in a person's pocket, would make the device easier to carry and more likely that the user will have it on their person when needed. An example of such a device package, purely for the purpose of comparison, could be sized similarly to that of a USB "thumb drive" which is designed to be with users on a fairly constant basis. For example, one auto-injector device embodiment has dimensions of 3"×1"×0.5". Dimensions of auto-injector/mixing systems may vary, however these systems may be reduced in size as the microfluidic mixing assemblies used therein are smaller in size. The microfluidic channels also reduce the amount of potential waste volume that is not utilized, which also reduces the volume of interior chambers storing wet components.

One embodiment of an auto-injector device includes placing wet medicament into microfluidic channels of a MEMS device and freeze drying or lyophilizing the medicament into a dry substance. Attached to this MEMS device is a chamber containing a wet substance or diluents configured to interact with the dry medicament in desired proportions and in some cases being pH optimized. Thus having the ability to create a medicament of a desired potency as discussed above. The microfluidic channels aide in properly homogenizing the dry and wet components into a desired solution. The auto-injector may also include a mechanism either mechanical or electro-mechanical that controls the amount of mixing, thus controlling the dosage of the medicament delivered to a person. This simplifies the manufacturing process as one auto-injector may be manufactured for persons requiring a variety of medicament dosages. The dosage amount may be preset on the manufacturing side or controlled manually on the auto-injector. Once the solution is properly mixed in the MEMS device it can then be delivered via a hollow needle or through a needleless system.

In one configuration, multiple microfluidic channels exist in the mixing assembly, each with a dry component stored therein. A separate valve from the seal or valve containing the wet component in an interior chamber is placed to allow the wet component when activated to flow through one or multiple channels, thus increasing or decreasing the dosage desired. For instance, this separate valve in the mixing assembly may be magnetically controlled and a pharmacist or other manufacturer adds a magnet having a certain polarization which allows the valve to be open or closed, thus the same injection device may be used on multiple persons, with the dosage being externally modified or set. Other ways including a more physical setting (opening or closing) of the separate valve. It is within the scope to have more than two dosage settings. For embodiments, where the dry component is stored in wells or reservoirs prior to entering the mixing channels controllable valves may be open or close each of these wells or reservoirs, thus having a need for only one mixing channel.

In another configuration similar to those shown in FIGS. 1A-I a dual needle assembly system, each connected to a mixing assembly and interior chamber for storing a wet component of a medicament are all activated and actuated by a single stored energy source such as a compressed spring. For certain applications having two medicaments in a single device (that may not be readily mixed or stored in a single dry component) is useful. Thus, having a single stored energy source activate the seals for each interior chamber and send the respective wet components into the respective mixing assemblies where they are to be delivered via the needle assemblies. Thus a person or animal can receive two critical medicaments simultaneously.

One way to miniaturize the device is simply enabled by using micro fluidics as opposed to macroscopic components in the device design and/or device build. In addition, current epinephrine filled auto injectors store ~2 ml of drug in the vial purely for the purpose of maintaining the drugs stability, even though only ~15% of this drug actually makes it into the patient. By gaining enhanced drug stability from the dry and/or lyophilized component, we can potentially reduce the volume of fluid in the device by 85%, further enabling a smaller more compact and/or portable design. In some embodiments, the volume of the diluent storage is less than 5 ml, less than 2 ml of fluid, less than 1 ml of fluid and/or less than 0.5 ml of fluid as the actual volume of diluent required may also be less than 5 ml, less than 2 ml, less than 1 ml and in some cases less than 0.5 ml. Dry component mass for various medicaments can range upwards of 200 milligrams or more, but may also be less than 0.5 mg, less than 0.3 mg, less than 0.1 mg.

A wet/wet auto-injector device is also contemplated having a housing containing two interior chambers configured to store wet components that are contained by a sealing component(s) until activated wherein both wet components enter into a mixing assembly, such as those described above comprising at least one channel configured to cause chaotic flow, thus facilitating mixing of the two wet components. The wet components are then forced into a delivery system to be delivered into a person. The two interior chambers may be two compartments of a single collapsible bulb, two separate collapsible bulbs, or two individual chambers that may or may not be collapsible.

Another embodiment of the present invention comprises building into the auto injector and/or attached to the auto injector, and/or part of an enclosure that surrounds the auto injector like a case and/or pouch an alert mechanism that notifies or alerts the auto injector user and/or owner of extreme temperature the auto injector has been exposed to or is currently being exposed to. This could be done by visual and/or audio and/or vibratory queues and/or electromagnetic-based communication with the user's mobile devices and/or computers and/or computer networks. The device could also perform calculations to understand the amount of hot and/or cold being imparted onto and/or into the auto injector over time to estimate how the temperature extremes could impact the shelf life of the device. This could help signal the owner and/or user of the device that the epinephrine and/or medication and/or drug and/or antidote and/or auto injector needs to be replaced.

For example, a temperature strip that records these temperature excursions over time and activates a small blinking LED and/or "chirp" that goes off, similar to that of a smoke detector when the battery needs to be changed, could warn an individual that the device and/or epinephrine needs to be changed. This is an invention that could be used with current auto injectors based on a purely liquid drug as well as the invention described above based on auto-mixing of wet and dry component.

The above description is merely illustrative. Having thus described several aspects of at least one embodiment of this invention including the preferred embodiments, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A medicament mixing device comprising:
   a housing assembly having at least one interior chamber, the interior chamber including a wet compartment containing a wet medicament component;
   a seal structure placed within the wet compartment at an outlet orifice of the interior chamber, the seal structure being initially in a sealing condition that maintains the wet medicament component within the interior chamber, the seal structure being converted to a mixing condition as a result of activation of the device;
   a mixing assembly comprised of at least one microfluidic channel, in fluid communication with the interior chamber when the device is activated, the at least one microfluidic channel a) having a non-randomized predefined sidewall or b) providing a singular predefined flow path; and
   wherein a portion of the mixing assembly contains a dry medicament component within the at least one microfluidic channel, the dry medicament component configured to mix with the wet medicament component when the seal structure is converted to the mixing condition.

2. The mixing device of claim 1, further including internal structures contained within the microfluidic channel.

3. An automatic injection device containing a pre-loaded charge of medicament for automatically self-administering the medicament upon actuation thereof, the device comprising:
   a housing assembly having an interior chamber, the interior chamber including a wet compartment containing a wet medicament component;
   a seal structure placed within the wet compartment at an outlet orifice of the interior chamber, the seal structure being initially in a sealing condition that maintains the wet medicament component within the interior chamber, the seal structure being converted to a mixing condition as a result of activation of the device;
   a mixing assembly comprised of at least one microfluidic channel, the at least one microfluidic channel a) having a non-randomized predefined sidewall or b) providing a singular predefined flow path, the microfluidic channel being in fluid communication with the interior chamber when the device is activated, and wherein the mixing assembly contains a dry medicament component contained within the at least one microfluidic channel configured to mix with the wet medicament component when the seal structure is converted to the mixing condition;

a delivery assembly that dispenses a charge of medicament comprised of the mixed wet medicament component and the dry medicament component from the housing assembly;

an activation assembly carried by the housing assembly and including a stored energy source, wherein activation of the activation assembly releases the stored energy from the stored energy source, and wherein the release of the stored energy causes a) the seal structure to be converted from the sealing condition to the mixing condition and thereby permit the wet medicament component to pass there through, b) the wet medicament component to be forced through the mixing assembly to facilitate mixing of the wet and dry medicament components thus forming the charge of medicament, and c) the charge of medicament to be forced through the delivery assembly.

4. The automatic injection device of claim 3, wherein the dry medicament component is partially soluble in the wet medicament component.

5. The automatic injection device of claim 3, wherein the microfluidic channel of the mixing device includes a plurality of grooves formed therein, wherein said grooves facilitate chaotic flow when a wet component flows by said grooves.

6. The automatic injection device of claim 3, wherein the one or more microfluidic channels of the mixing assembly include a plurality of bends.

7. The automatic injection device of claim 3, wherein the microfluidic channel of the mixing device includes internal structures.

8. The automatic injection device of claim 3, further including a homogenizing region in fluid communication with, and having a larger cross section than, the mixing assembly.

9. The automatic injection device of claim 3, wherein the dry medicament component contained within a portion of the one or more microfluidic channels contain a lyophilized dry medicament.

10. The automatic injection device of claim 9, wherein the lyophilized dry medicament is an epinephrine component or any salt-based form thereof.

11. The automatic injection device of claim 3, wherein the mixing assembly includes two or more microfluidic channels.

12. The automatic injection device of claim 3, further including a safety cap removably inserted into the housing assembly, wherein the device may not be activated until the safety cap is removed from the housing assembly.

13. The automatic injection device of claim 3, wherein the stored energy source is a compressed spring.

14. The automatic injection device of claim 3, wherein the interior chamber is configured to collapse upon activation.

15. The automatic injection device of claim 3, further including a trigger assembly configured to release the stored energy source when activated.

16. The automatic injection device of claim 3, wherein a cross-section of the one or more microfluidic channels is less than two millimeters across in one dimension.

17. The automatic injection device of claim 3, wherein a cross-section of the one or more microfluidic channels is less than one millimeter across in one dimension.

18. The automatic injection device of claim 3, wherein no dimension of a cross-section of the one or more microfluidic channels is greater than a millimeter across.

* * * * *